United States Patent [19]

Daikuzono

[11] Patent Number: 5,050,597
[45] Date of Patent: Sep. 24, 1991

[54] LASER IRRADIATION SYSTEM FOR THERMOTHERAPY

[75] Inventor: Norio Daikuzono, Ichihara, Japan

[73] Assignee: S.L.T. Japan Co., Ltd., Japan

[21] Appl. No.: 505,077

[22] Filed: Apr. 5, 1990

Related U.S. Application Data

[63] Continuation of Ser. No. 163,925, Mar. 4, 1988, abandoned.

[30] Foreign Application Priority Data

Mar. 5, 1987 [JP] Japan .................... 62-50723

[51] Int. Cl.$^5$ .................... A61N 5/06; A61F 7/00
[52] U.S. Cl. .................... 128/395; 128/398; 128/399; 606/1; 606/10; 606/11
[58] Field of Search .............. 128/395, 398, 400, 401, 128/399; 606/1, 10, 11, 12, 13, 16

[56] References Cited

U.S. PATENT DOCUMENTS

| | | | |
|---|---|---|---|
| 4,397,314 | 8/1983 | Vaguine | 128/399 |
| 4,580,557 | 4/1986 | Hertzmann | 606/12 |
| 4,601,037 | 7/1986 | McDonald | 128/395 |
| 4,719,919 | 1/1988 | Marchosky et al. | 128/401 |
| 4,736,743 | 4/1988 | Daikuzono | 128/398 |

FOREIGN PATENT DOCUMENTS

| | | | |
|---|---|---|---|
| 0130950 | 1/1985 | European Pat. Off. | 128/395 |
| 2740969 | 3/1979 | Fed. Rep. of Germany | 128/398 |
| 3720742 | 1/1988 | Fed. Rep. of Germany | 128/395 |

OTHER PUBLICATIONS

Brody, Herb, "Laser Light Kills Marked Tumors", High Technology, Nov. 1984, p. 76.

N. Daikuzono et al, "The Application of YAG Laser to Hyperthermia", Journal of Nihon Laser Igaku-kai, vol. 6, No. 3, (Jan. 1986), pp. 71-76.

Thomas J. Dougherty, "Photoradiation Therapy for the Treatment of Malignant Tumors", Cancer Research vol. 38, (Aug. 1978), pp. 2628-2635.

Shihro Mashiko et al, "Basic Study on Photochemical Effect of Pheophorbide A Irradiated by NO:YAG Laser Light", Journal of Nihon Laser Igaku-kai, vol. 6, No. 3 (Jan. 1986), pp. 113-116.

N. Daikuzono et al, "Endoscopic Local Hyperthermia with Nd-YAG Laser—Experimental Study and Development of Computed Thermo-System", Journal of Nihon Laser Igaku-kai, vol. 6, No. 3 (Jan. 1986), pp. 347-350.

*Primary Examiner*—William H. Grieb
*Assistant Examiner*—Jessica J. Harrison
*Attorney, Agent, or Firm*—Lowe, Price, Leblanc and Becker

[57] ABSTRACT

Laser thermotherapy apparatus including a laser splitter which branches laser energy from a laser source to laser guides or optical fibers, each guide having an emitting end. First and second switches are positioned, respectively, before the splitter and in the individual laser guides. Temperature sensors are provided to sample the temperature of living tissue located adjacent each guide emitting end. A controller turns the respective switches on and off in response to the sensed temperature thereby to maintain a predetermined, selectable tissue temperature.

15 Claims, 8 Drawing Sheets

LASER IRRADIATION SYSTEM FOR THERMOTHERAPY

This application is a continuation of application Ser. No. 163,925 filed Mar. 4, 1988, now abandoned.

BACKGROUND OF THE INVENTION

This invention relates to a laser irradiating apparatus for thermotherapy.

Recently, laser beam application to a medical field has been exploited remarkably. Similarly, (local) thermotherapy has been put into the limelight as an effective therapy for cancer recently. According to this therapy, laser beam is irradiated for 10 to 25 minutes to keep a cancer tissue at a temperature of 42° to 44° C. for letting the tissue die. The effectiveness of this therapy has been reported, by N. Daikuzono (inventor of the present invention) et al in the journal of Nihon Laser Igaku-kai, Vol. 6, No. 3 (Jan. 1986), pp. 71 to 76 and pp. 347 to 350.

In this case, a single probe is used for emitting laser beam generated by a laser beam generator and it is inserted in a tissue to be treated, while the laser beam is irradiated from the probe. At the same time, to keep the tissue temperature at a temperature of 42° to 44° C., a tip end of a temperature sensor paired with the probe is also inserted in the tissue to measure the tissue temperature and control the on-off operation of a shutter provided in a laser beam guide system which connects the laser beam generator and the probe.

On the other hand, Dougherty et al reported in 1978 about this therapy that when hematoporphyrin derivatives (HpD) were injected intervenously and weak beam of argon laser or argon pigment laser was irradiated after 48 hours, said HpD generated a first-order oxygen to show a strong carcinostatic activity. This therapy has then been watched and many researches have been reported, including a report in the journal of Nihon Laser Igaku-kai, Vol. 6, No. 3, pp. 113 to 116. It has also been known that pheophobide a is employable as a photoreactive agent. As a laser beam, there has been used YAG laser.

SUMMARY OF THE INVENTION

However, in the conventional local thermotherapy, a single pair of laser beam probe and temperature sensor is employed. Therefore, a temperature distribution in the tissue caused by laser beam irradiation forms a convex around the probe as shown in FIG. 10. If the central portion is kept at the temperature range as specified above, the treatment might be effective only for the central portion and it might not effective possibly for the portions remote from the center. By this reason, the treatment should be carried out at various points. However, since the operating time is limited, the treatment can be given only to a limited portion. Moreover, the temperature control is effected on the basis of the temperature of the tissue at a position different from that of the probe, which temperature differs from the temperature of the center of the temperature distribution. This makes the temperature control of the living tissue very difficult.

It is therefore an object of the present invention to provide a laser beam irradiation system which is capable of effecting thermotherapy for a wide region by one-dose laser beam irradiation and capable of obtaining a substantially flat temperature distribution, which assures full treatment over the region to be treated without leaving untreated portions.

It is another object of the present invention to provide a system which is capable of effecting a photochemical reaction in combination.

To solve the problems as described above and to achieve the objects as described above, the first invention features a laser irradiation system for thermotherapy which comprises laser beam guides for guiding laser beam to a plurality of laser beam emitting ends; laser beam switching means provided in the respective guides; temperature sensing means provided in combination with the respective laser beam emitting ends for detecting temperatures of a living tissue; and on-off control means for controlling said switching means, separately, in response to tissue temperature signals from the temperature sensing means, respectively.

The second invention features a laser irradiation system for thermotherapy which comprises laser beam guide means through which a laser beam is branched to a plurality of laser beam emitting ends; a first switching means provided in the laser beam guide means at its position before branching to change the laser beam into a regular pulsive beam; second switching means provided in the laser beam guide means after branching; temperature sensing means provided in combination with the respective laser beam emitting ends for detecting temperatures of a living tissue; and on-off control means for controlling said second switching means, separately, in response to tissue temperature signals from the temperature sensing means, respectively.

Further, the third invention features a laser irradiation system for thermotherapy which comprises laser beam guide means through which a laser beam is branched to a plurality of laser beam emitting ends; a first switching means provided in the laser beam guide means at its position before branching to change the laser beam into a regular pulsive beam of small pulse duration; a power meter provided between said first switching means and the branching point for detecting an intensity of laser beam to be guided into respective branches, based on the total amount of pulsive beam per unit time; temperature sensing means provided in combination with the respective laser beam emitting ends after the branching for detecting temperatures of a living tissue; and on-off control means for controlling said second switching means, separately, in response to tissue temperature signals from the temperature sensing means respectively, while receiving a laser beam intensity signal from said power meter.

The fourth invention features a laser irradiation system for thermotherapy which comprises laser beam guide means through which a laser beam is branched to a plurality of laser beam emitting ends; a first switching means provided in the laser beam guide means at its position before branching to change the laser beam into a regular pulsive beam of small pulse duration which is capable of providing a high peak sufficient to cause a photochemical reaction; a power meter provided between said first switching means and the branching point for detecting an intensity of laser beam to be guided into respective branches, based on the total amount of pulsive beam per unit time; temperature sensing means provided in combination with the respective laser beam emitting ends after the branching for detecting temperatures of a living tissue; and on-off control means for controlling said second switching means, separately, in response to tissue temperature signals from the temperature sensing means, respectively, while receiving a laser beam intensity signal from said power meter.

In the present invention, a plurality of pairs of laser beam emitting ends, for example, laser beam emitting probe and temperature sensor are provided so that laser beam can be irradiated onto a living tissue to be treated, simultaneously from the plural probes. Therefore, the region to be treated by one-dose irradiation can be widened and the treating time can be curtailed accordingly.

A laser beam switching means is provided in each of guides for guiding laser beam to the respective probes on the one-to-one basis. Each switching means is controlled separately in response to a temperature signal of a living tissue output from a temperature sensor which is directly coupled or associated by some means with the probe. Thus, the irradiation energy to be given to each portion of the tissue is controlled on the basis of the momentary temperature of said portion of the tissue, so that the heat generated there may be equal to those of other portions of the tissue under treatment. As a result of this, the temperature distribution over the region under the treatment on the basis of the total energy irradiation may become flat. For example, when three probes P1 to P3 are disposed as illustrated in FIG. 9, the total temperature distribution will be as shown by T, which is formed of respective temperature distribution T1 to T3 each having a peak and developed by energy irradiated from each of the three probes P1 to P3. Thus, substantially flat temperature distribution can be obtained over a wide range.

In contrast, if the on-off control of laser beam is not carried out for the respective guides, the total temperature distribution will be as shown by T′ in FIG. 11, mainly because of differences in blood stream amount between the portions of the tissue under treatment, or possibly because of differences in shapes or surface conditions between the probes. Thus, the temperature distribution will be so uneven that even when the tissue temperature at some portion is within a temperature range of 42° to 44° C., the tissue temperatures at other portions are not always within the range. In this case, the thermotherapy can exert its effect only at a part of the region to be subjected to the treatment. Therefore, if the treatment is carried out, while overlooking this problem, some portions may possibly remain untreated.

In the present invention, plural pairs of probe and temperature sensor are provided. Therefore, the tissue temperatures can be detected at respective portions of the tissue, which may be different due to differences in laser beam absorption amounts between the portions of the tissue possibly caused by differences in blood stream amounts between the portions of the tissue. As a result of this, the switching means may be controlled for the respective guides corresponding to the portions of the region, respectively. Thus, the tissue temperatures of the respective portions of the region may be controlled so as to be within a desired temperature range. In contrast, if the laser beam energy given to the tissue through the guides is controlled in common by a switching means, based on the temperature detection at only one portion of the tissue, the temperatures can not always be controlled appropriately and it might be higher or lower than the desired temperature range, because of the differences in blood stream amounts between the portions.

In a further preferred form of the present invention, thermotherapy is carried out in combination with a medical treatment by a photochemical reaction, using a single laser beam generator, which has never been practiced before. The laser beam suitable for the photochemical reaction is preferably a pulsive laser beam having a pulse duration of about 10 nanosec and having an exciting energy as large as 10 mJ as a fundamental wave of 1.064 um wavelength and 0.5 mJ as a subharmonic wave (SH wave) of 532 nm wavelength By this reason, the Q-switch and the Q-switch controller are provided at the laser beam guide before branching of the laser beam guide to control a peak length and the duration of the pulse for obtaining such pulsive laser beam. This enables the laser beam emitting ends of the respective guides to irradiate laser beam optimum for the photochemical reaction, causing two-photon absorbing reaction sufficiently within the tissue.

It will be a key how to control the switching means in the respective guides for controlling the pulsive laser beam by using the Q-switch. The power meter is then provided between the Q-switch and the branching point of the guides, so that the intensity of the laser beam is obtained in terms of integration of small pulses and the switching means in the respective guides are controlled according to the temperature detection signals, on the basis of the laser beam intensity. Therefore, even if the photochemical reaction is used in combination, the tissue temperatures in the treatment of the thermotherapy can be controlled appropriately.

DESCRIPTION OF THE PREFERRED EMBODIMENT

The invention will now be described in detail.

Figure 1:
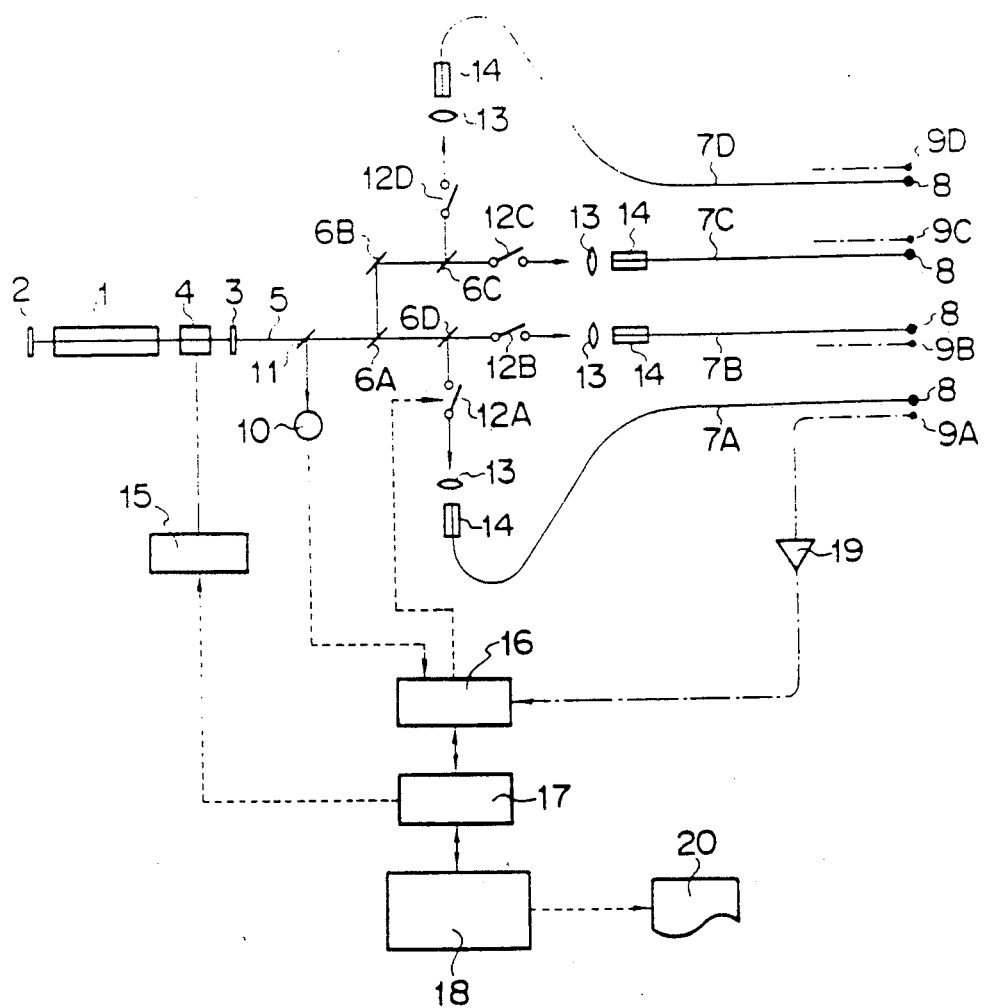
FIG. 1 is a schematic view showing the entire system of the present invention.

Referring now to FIG. 1 which schematically shows a system of the present invention, 1 is a laser medium, for example, a laser rod of YAG or ND:YAG. Full reflectors 2 and 3 are provided coaxially with the laser rod 1 to form a laser resonator. A Q-switch 4 is provided between the laser rod 1 and the reflector 3. In such a laser generating apparatus, an electric energy is applied to the laser rod 1 from a pumping means (not shown) so that the laser rod 1 radiates continuous wave (CW) laser beam. With this respect, the laser beam led to a main guide 5 is made pulsive due to the provision of the Q-Switch 4. This pulsive laser beam employable in the present invention has preferably high peaks of 30 W or more, so as also to cause a photochemical reaction.

The main guide 5 is branched into, for example, four branch guides 7A, 7B, 7C and 7D by mirrors 6A, 6B, 6C and 6D. Each of the branch guides 7A, 7B, 7C and 7D has, at its respective tip end, a probe 8 at which the laser beam emits The main guide 5 and the branch guides 7A to 7D are each made of a flexible optical fiber 7 and the probe 8 is provided at each of the tip ends of the respective optical fibers coaxially therewith. Of course, the tip end of the optical fiber itself may be used as a laser beam emitting end, but it is preferred to employ the probe to puncture a tissue. Temperature sensors 9A to 9D each comprising a thermocouple are provided for the respective branch guides 7A to 7D and/or probes 8, 8 . . . at positions adjacent to the probes, respectively.

10 is a power meter provided in the main guide 5 for detecting an intensity of laser beam taken by the mirror 11. The branch guides 7A to 7D have switches 12A to 12D constituting second switching means, respectively 13 and 14 are a laser beam transmitting lens and a light-receiving intermediate end, respectively.

15 is a switch controller, 16 is an AD converter, 17 is an interface, 18 is a central processing unit (CPU), 19 is an amplifier and 20 is a display such as a printer.

Figure 3:
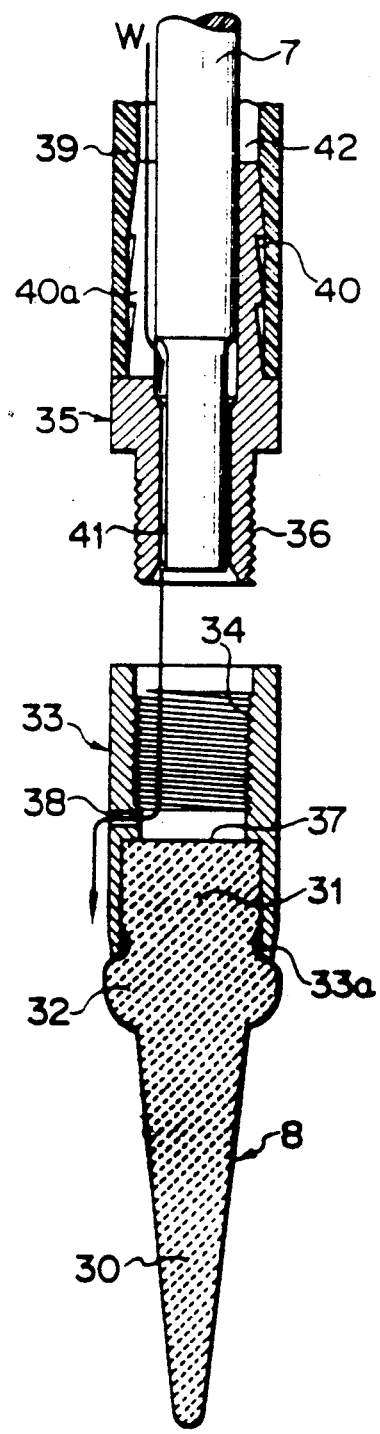
FIG. 3 is a longitudinal cross sectional view of an example of laser beam emitting end structure.
Figure 4:
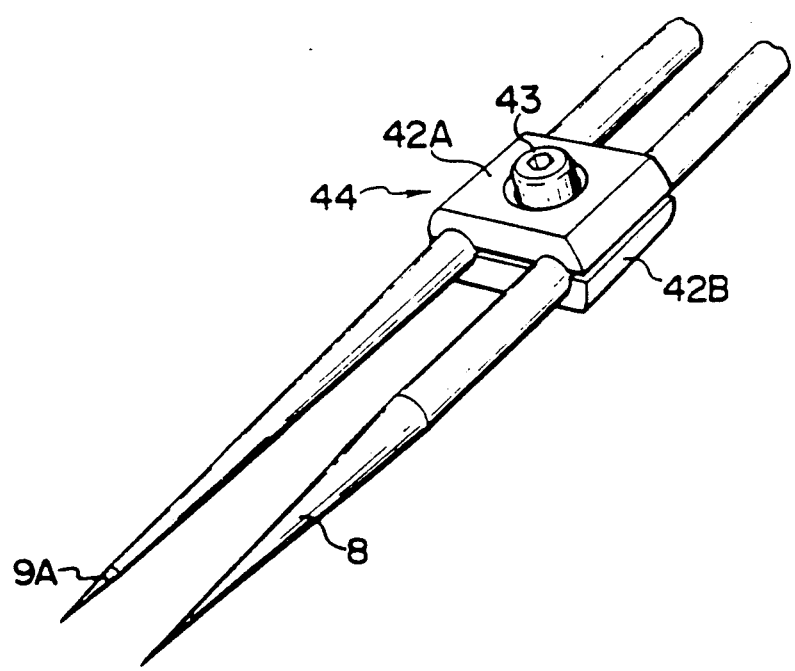
FIG. 4 is a perspective view showing the coupling of a probe and a temperature sensor.

An example of a particular configuration of the probe 8 is as illustrated in FIG. 3. The probe 8 may preferably be made of a laser-transmittable material such as natural or artificial sapphire, quartz, diamond, or other natural or artificial ceramic material. Or, the probe 8 may be made of some polymeric material. The probe 8 is preferably comprised of a tapering conical puncturing portion 30, a fixing portion 31 and a flange portion 32 provided therebetween. This probe 8 is integrally coupled to a female connector 33 in such a manner that the fixing portion 31 is fitted in the cylindrical female connector 33 and a coupling portion 33a of the female connector is caulked or glued with a ceramic thermoresistance adhesive or both caulked and glued. The female connector 33 has an inner surface formed with a female thread 34, which is disengageably mated with a male thread 36 of a male connector 35. For example, two (only one of which is shown in the example as illustrated) openings 38 for cooling water, which communicate with both the inside and the outside of the connector, are provided at a position adjacent to a light receiving end 37 of the probe 8, at angular intervals of 180' in the circumferential direction.

On the other hand, a male connector 35 is pressedly fitted into a flexible tube 39, for example, made of Teflon (Trade name). In this press fitting, a stepped portion 40 formed at a base end portion of the male connector 35 serves to prevent the male connector 35 from slipping from the tube easily.

The optical guide 7 for laser beam is led into the tube 39 and the male connector 35 so as to extend therealong. A cooling-water path 41 is formed between the optical guide 7 and the tube 39. A tip end portions of the optical guide 7 is generally closely fitted to the inner surface of the male connector at its stepped portion 40, while leaving two slits 40a formed at diametric positions of the stepped portion 40 to allow cooling-water to pass therethrough. The cooling water path 41 is further formed between the inner surface of the tip end portion of the male connector 35 and the outer surface of the optical guide 7.

Such a laser beam emitting tip assembly with the female connector 33 threadably engaged with the male connector 35 is fitted within an endoscope or some suitable holder. In the so assembled state, pulsive laser beam enters, from the light receiving end 37, into the probe 8 and it is irradiated from all over the external surface of the punctuaring portion 30. At this time, cooling-water W cools the probe 8 while passing through the path 42, slits 40a and path 41 and it flows out through the openings 38 onto the surface of the tissue to cool the tissue M.

Figure 5:
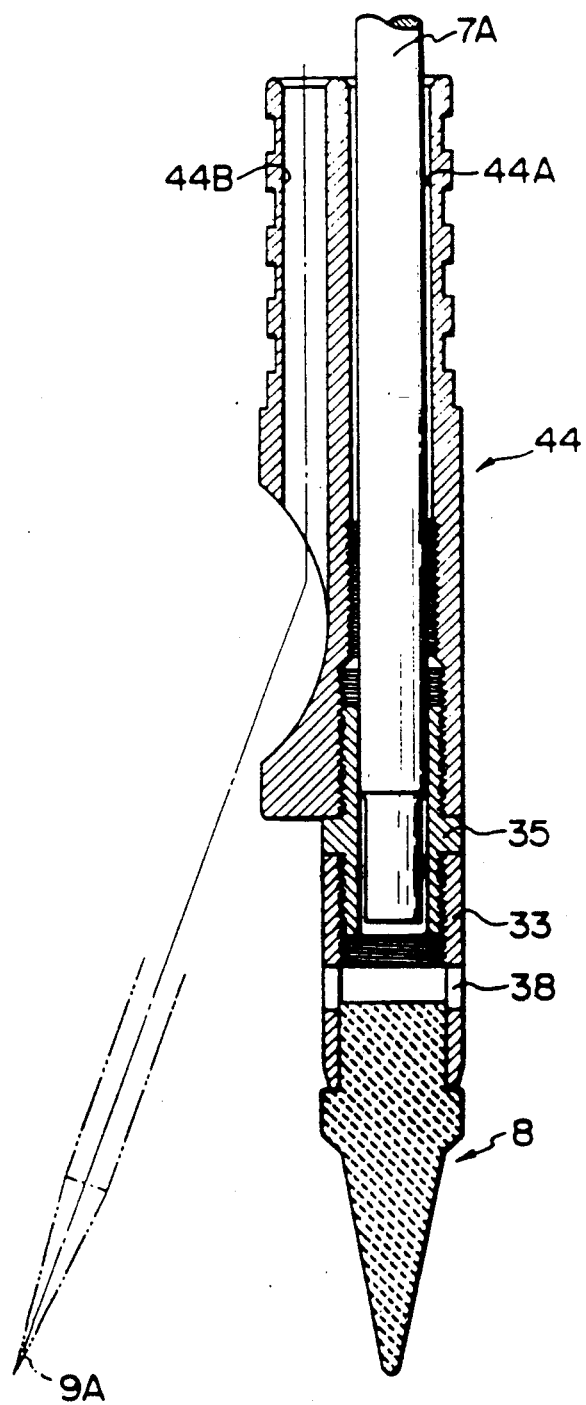
FIG. 5 is a longitudinal sectional view of another example of laser beam emitting end structure.
Figure 6:
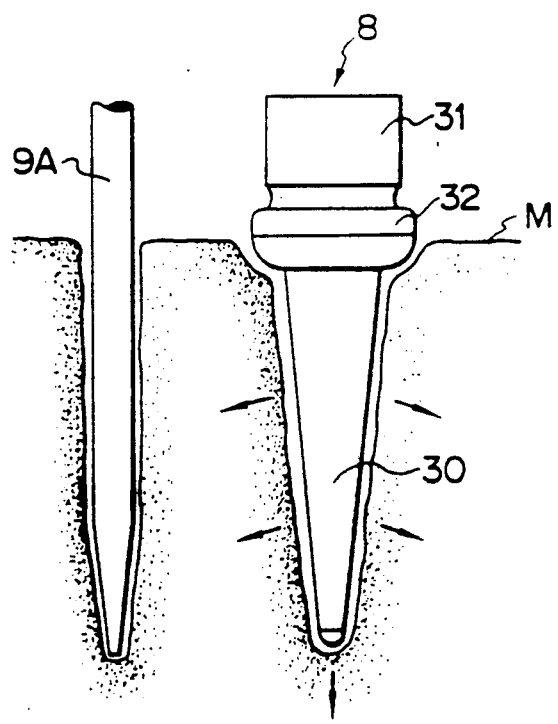
FIG. 6 is a sectional view showing the probe as the laser beam emitting end and the temperature sensor which are inserted into the tissue.

For this laser beam emitting tip assembly, each of the temperature sensors 9A to 9D is provided on the one-to-one basis. In this case, the assembly and the temperature sensor may be coupled with a holder 44 which comprises a pair of coupling members 42A, 42B and a small coupling bolt for fastening them. In the arrangement as illustrated, the guide is held by some suitable holder (not shown) on a stand (not shown) installed on the ground. However, the couple of the assembly and the temperature sensor may be held by a two-hole loading tube 44 as illustrated in FIG. 5. In FIG. 5, parts or portions similar to or same as the parts or portions of FIG. 3 are denoted by similar or same numbers, and the optical guide 7 is fitted in a first hole 44A of the two-hole holding tube 44 and a conductor of the temperature sensor 8 is fitted in a second hole 44B thereof.

Figure 7:
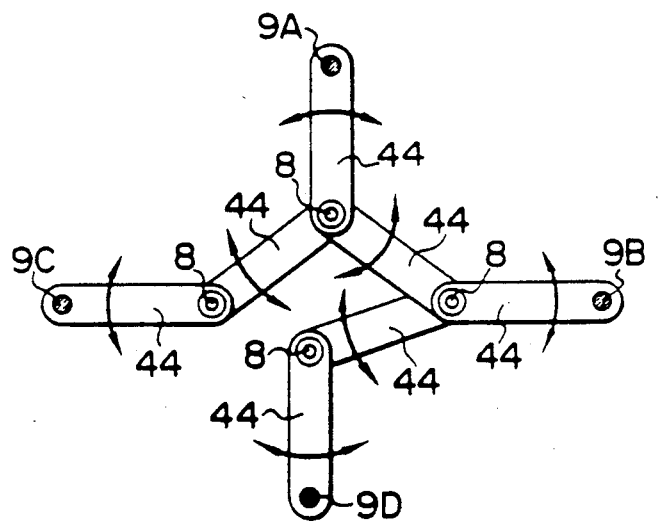
FIG. 7 is an explanatory view showing the positioning of the probes and the temperature sensors.

The holder 44 is operative to determine a spaced distance between the probes 8 and the respectively coupled temperature sensors 9A to 9D. Moreover, a plurality of holders 44 may be employed as illustrated in FIG. 7, in which the positions of the probes 8 and the temperature sensors 9A to 9D may be selectively determined by rotatably positioning, around a center axis of one probe, center axes of the other probes through the respective holders 44.

Referring again to FIG. 1 together with FIG. 2, a temperature control of a tissue will now be described. First, the Q-switch controller 15 is operated to set the level and the duration of the pulse and then laser beam is irradiated to raise the temperature of the tissue gradually. Thereafter, when the temperature of the tissue reaches 42° C., which is detected by a signal from the temperature sensor, (a period before the time is shown as A in FIG. 2), for example, a switch 12A in the guide A is opened to stop the transmission of the beam to the probe 8. After a given time period, the switch 12A is closed again and thereafter the switch 12A is opened once again, thus repeating the on-off of the switch 12A. The short duty cycle in this B period may be controlled according to a momentary temperature signal from the temperature sensor 9A or temperature rise with time, on the basis of a momentary intensity of laser beam output from the power meter. Thereafter, when the tissue temperature reaches a predetermined point, for example, the upper limit 44° C. (C period), the switch 12A is kept opened to allow the tissue temperature to be lowered. Then, when the tissue temperature is lowered to below the lower limit 42° C. (D period), the switch 12A is kept closed to let the tissue temperature rise. In a period E where the tissue temperature returns to 42° C., temperature rise is controlled by controlling the duty cycle through short and quick on-off control. In a period F where the tissue temperature reaches the upper limit 44° C., the switch is kept off. This sort of control for the first switching means, namely switch 12A is further repeated and similar control is also effected with respect to each of the B, C and D system.

This control is implemented according to the instructions from the central processing unit 18 having a program preliminarily incorporated therein.

Normally, the Q-switch is kept in a given mode throughout one medical treatment. However, the medical treatment is applied over different parts or different organs, the Q-switch controller 15 is operated to change the wavelength and duration of the oscillation pulse. After this changing, the on-off timing of the duty cycle control in the periods B and E is changed. For example, if the intensity of the laser beam output from the power meter 10 is high, the temperature rise is fast so that the on-time is shortened and the off-time is lengthened in the period B and E.

Figure 2:
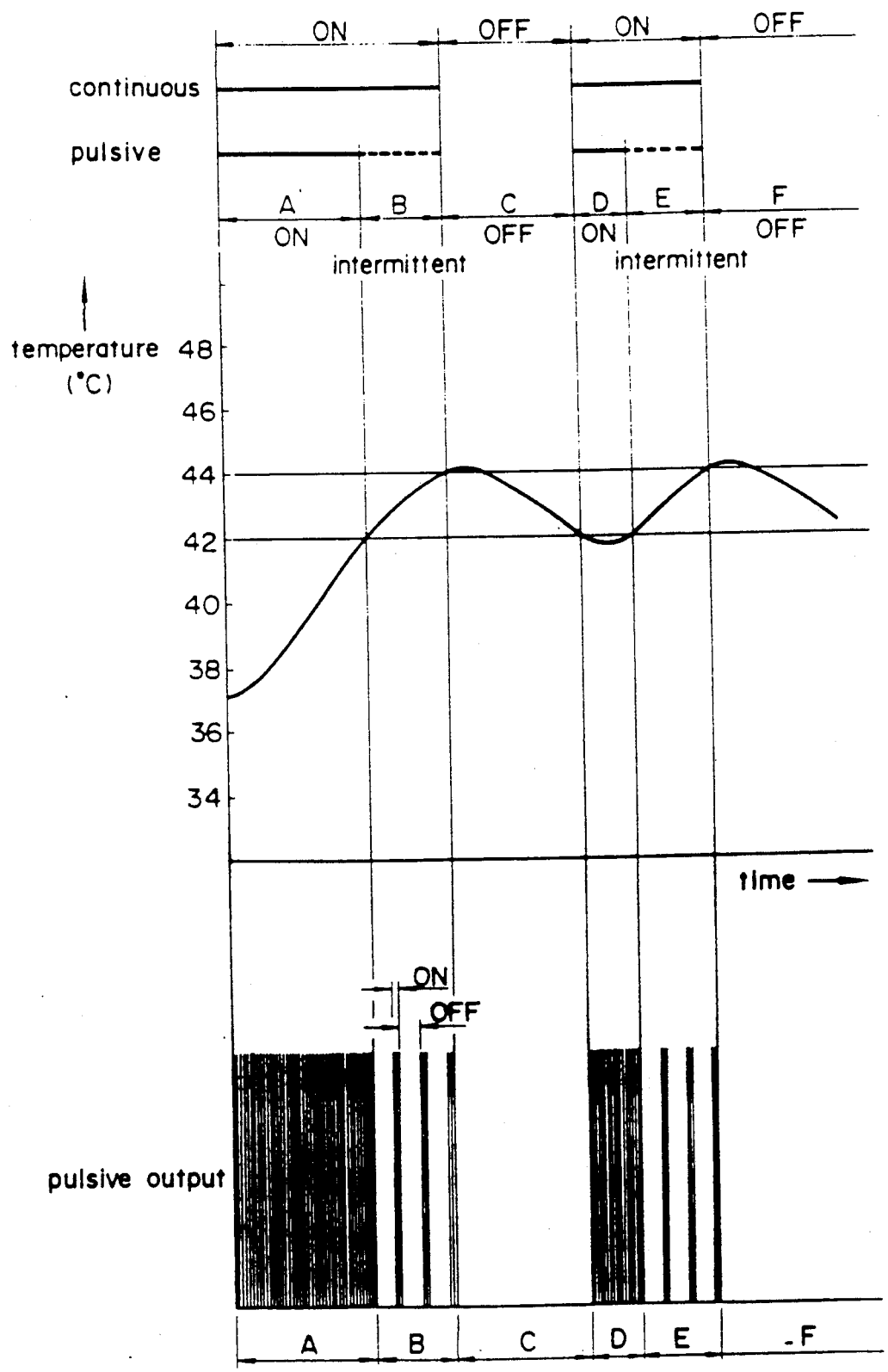
FIG. 2 is an explanatory view showing the control for a tissue temperature.

Although the above explanation refers to the pulsive oscillation, the present invention may alternatively employ a continuous oscillation as shown in FIG. 2. In this case the periods 1A and B are of on-time, the period C is of off-time, the periods D and E are of on-time and the period F is of off-time. Essentially, the Q-switch is not needed.

However, it is to be noted that the photochemical reaction can not be used in combination with this continuous oscillation method. Moreover, in the continuous oscillation method, such an ideal temperature change curve as shown in FIG. 2 is hardly obtained and the upper and/or lower limit may possibly be overshot. By these reasons, the continuous oscillation method is not always preferable.

Figure 8:
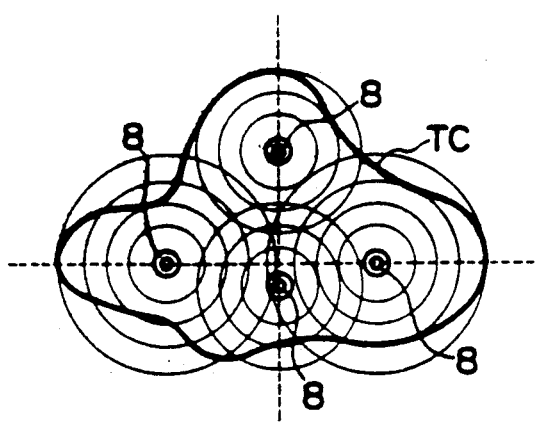
FIG. 8 is an explanatory view showing an example of equithermic distribution under the probes.
Figure 9:
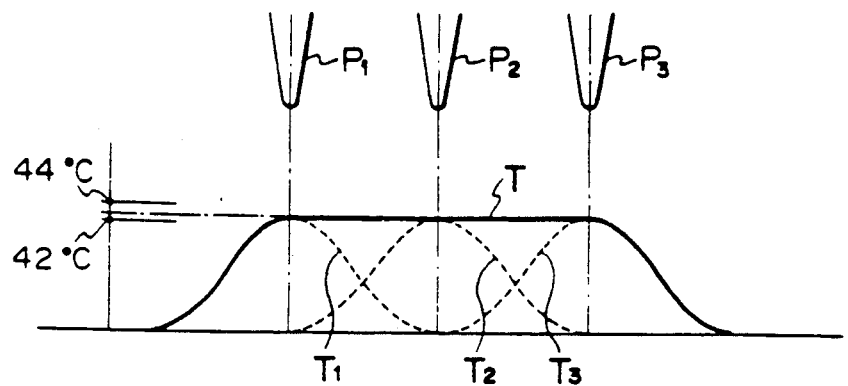
FIG. 9 is a temperature distribution diagram according to the present invention.
Figure 10:
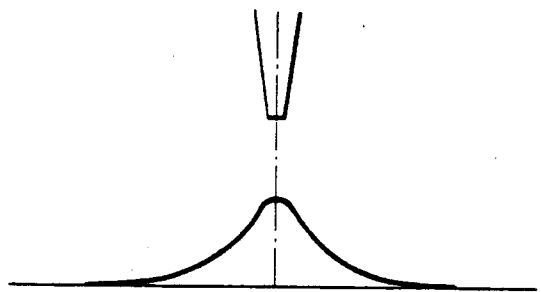
FIG. 10 is a temperature distribution diagram according to the conventional technique.
Figure 11:
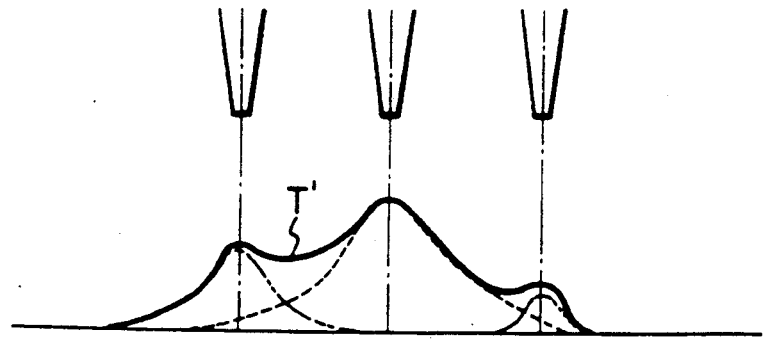
FIG. 11 is a temperature distribution diagram for a reference.

FIG. 8 shows an example of positional arrangement of probes 8, 8 . . . and an example of isothermic distribution curves TC. From this figure, it can be seen that the isothermic distribution curves TC are ideally formed around the respective probes 8, 8 . . . . Furthermore, the irradiation energy and therefore the heat given to the tissue may be controlled around the probes 8 (PI to P3), so that a flat temperature distribution T may be obtained. In contrast, a desired effect of thermotherapy can hardly be obtained as shown by a temperature distribution T' even if the energy is irradiated widely.

The pulse oscillation method is advantageous because it enables photochemical reaction together with thermotherapy as described above. However, when only the thermotherapy is required, one laser generating apparatus will suffice if a main guide of the laser beam is branched into branch guides to provide continuous waves. Or, a plurality of laser generating apparatuses may be provided to lead the laser beam directly to the laser emitting ends without providing guide braces, so that laser beam is irradiated from the laser beam emitting ends corresponding to the plural laser generating apparatuses for carrying out a thermotherapy. Of course, switching means are provided at the respective laser guides in this case, too. The on-off control of the switching means may be of a continuous method or a pulsive method.

As described above, according to the present invention, not only the region to be covered by one medical treatment can be widened, but also the treatment of such a wider region can be effected with an even temperature distribution, irrespective of local conditions of the tissue such as an amount of blood stream.

When pulsive laser beam is oscillated from the laser generating apparatus, a photochemical reaction together with a thermotherapy may be attained.

What is claimed is:

1. A laser irradiation system for thermotherapy which comprises laser beam guides for guiding laser beams from laser source means to a plurality of laser beam emitting ends; laser beam switching means in the respective guides; temperature sensing means associated with the respective laser beam emitting ends for detecting temperatures of living tissue and for generating a temperature signal representative of said detected temperature; on-off control means for separately controlling said switching means in response to tissue temperature signals from respective associated temperature sensing means.

2. A laser irradiation system according to claim 1 wherein said laser beam emitting ends, temperature sensing means and switching means are arranged to create a region of substantially even temperature in living tissue between laser beam emitting ends.

3. A laser irradiation system according to claim 1 wherein the input from said laser source means to said laser beam guides is substantially uniform.

4. A laser irradiation system according to claim 1 wherein said laser beams comprise branches of a single laser beam.

5. A laser irradiation system according to claim 4 including switching means in said single laser beam.

6. A laser irradiation system according to claim 1 including holder means for said laser beam emitting ends and temperature sensing means, said holder means maintaining predetermined spacing between each laser beam emitting end and its respective temperature sensing means and permitting variation of spacing between laser beam emitting ends.

7. A laser irradiation system for thermotherapy which comprises laser beam guides connected to a common laser source and to a plurality of laser beam emitting ends, on-off laser beam switching means in the laser beam guides; temperature sensing means associated with said respective laser beam emitting ends for sensing temperature of living tissue adjacent said ends, said temperature sensing means being associated with said switching means in the laser beam guides for controlling said switching in response to temperature in living tissue adjacent associated laser beam emitting ends sensed by said temperature sensing means.

8. A laser irradiation system according to claim 7 wherein said laser beam emitting ends, temperature sensing means and switching means are arranged to create an area of substantially even temperature in living tissue between laser beam emitting ends.

9. A laser irradiation system according to claim 7 including switching means in said common laser source.

10. A laser irradiation system according to claim 7 wherein said common source comprises laser beam guide means and second switching means to control the laser beam therein.

11. A laser irradiation system according to claim 10 wherein said second switching means changes the laser beam into a regular pulsive beam of small pulse duration, and including a power meter between said second switching means and said guide means for detecting an intensity of laser beam to be directed into respective guide means based on the total amount of pulsive beam per unit time.

12. A laser irradiation system according to claim 10 wherein said second switching means is effective to change the laser beam into a regular pulsive beam of small pulse duration which provides a high peak sufficient to cause a photochemical reaction.

13. A laser irradiation system for thermotherapy which comprises laser beam guide means through which a laser beam is branched to a plurality of laser beam emitting ends; a first switching means provided in the laser beam guide means at its position before its branching to change the laser beam into a regular pulsive beam; second switching means provided in the laser beam guide means after its branching; temperature sensing means provided in combination with the respective laser beam emitting ends for detecting temperatures of a living tissue; on-off control means for controlling said second switching means, separately, in response to tissue temperature signals from the temperature sensing means, respectively.

14. A laser irradiation system for thermotherapy which comprises laser beam guide means through which a laser beam is branched to a plurality of laser beam emitting ends; a first switching means provided in the laser beam guide means at its position before its branching point to change the laser beam into a regular pulsive beam of small pulse duration; a power meter provided between said first switching means and the branching point for detecting an intensity of laser beam to be guided into respective branches, based on the total amount of pulsive beam per unit time; second switching means provided in the laser beam guide means after its branching; temperature sensing means provided in combination with the respective laser beam emitting ends after the branching for detecting temperatures of a living tissue; on-off control means for control said second switching means, separately, in response to tissue temperature signals from the temperature sensing means, respectively, while receiving a laser beam intensity signal from said power meter.

15. A laser irradiation system for thermotherapy which comprises laser beam guide means through which a laser beam is branched to a plurality of laser beam emitting ends; a first switching means provided in the laser beam guide means at its position before its branching point to change the laser beam into a regular pulsive beam of small pulse duration which provides a high peak sufficient to cause a photochemical reaction; a power meter provided between said first switching means and the branching point for detecting an intensity of laser beam to be guided into respective branches, based on the total amount of pulsive beam per unit time; second switching means provided in the laser beam guide means after its branching point; temperature sensing means provided in combination with the respective laser beam emitting ends after the branching for detecting temperatures of a living tissue; on-off control means for control said second switching means, separately, in response to tissue temperature signals from the temperature sensing means, respectively, while receiving a laser beam intensity signal from said power meter.

* * * * *